(12) United States Patent
Kuboshima

(10) Patent No.: US 8,101,730 B2
(45) Date of Patent: Jan. 24, 2012

(54) METHOD FOR SYNTHESIZING RARE-EARTH OXO ISOPROPOXIDE

(75) Inventor: Yoshinori Kuboshima, Tokyo (JP)

(73) Assignee: Kabushikikaisha Kojundokagaku Kenkyusho, Sakado-shi, Saitama (JP)

( * ) Notice: Subject to any disclaimer, the term of this patent is extended or adjusted under 35 U.S.C. 154(b) by 437 days.

(21) Appl. No.: 12/361,295

(22) Filed: Jan. 28, 2009

(65) Prior Publication Data
US 2009/0192301 A1    Jul. 30, 2009

(30) Foreign Application Priority Data

Jan. 29, 2008  (JP) ................................ 2008-017039
Nov. 18, 2008  (JP) ................................ 2008-294115

(51) Int. Cl.
*C07F 5/00*    (2006.01)
(52) U.S. Cl. ......................................................... 534/15
(58) Field of Classification Search ...................... 534/15
See application file for complete search history.

(56) References Cited

FOREIGN PATENT DOCUMENTS
JP            09-157272 A      6/1997

OTHER PUBLICATIONS

Poncelet et al. "Chemistry of yttrium triisopropoxide revisited. Characterization and crystal structure of Y5(.mu.5-O)(.mu.3-OPr-iso)4(.mu.2-OPr-iso)4(OPr-iso)5" Inorganic Chemistry, 1989, vol. 28, pp. 263-267.*

Simic et al. "Ring-Opening Polymerization of D,L-Lactide Using Rare-Earth μ-Oxo Isopropoxides as Initiator Systems" Macromolecules, 1997, vol. 30, pp. 7338-7340.*

Kritikos et al. "Synthesis, structure and characterisation of Ln5O(OPri)13 with Ln=Nd, Gd or Er" J. Chem. Soc. Dalton Trans., 2001, pp. 1931-1938.*

V. Simic et al., "Ring-Opening Polymerization of D,L-Lactide Using Rare-Earth u-oxo Isopropoxides as Initiator Systems", Macromolecules, 1997, pp. 7338-7340, vol. 30.

O. Poncelet et al., "Chemistry of Yttrium Triisopropoxide Revisited. Characterization and Crystal Structure of Y5(u5-O)(u3-OiPr)4(u2-OiPr)4(OiPr)5", Inorganic Chemistry, 1989, pp. 263-267, vol. 28.

T. Okano et al., Journal of Chemical Scoiety of Japan, 1993, pp. 487-492, vol. 5.

G. Westin et al., "Synthesis and Properties of Erbium Isopropoxides: Structural Characterization of Er5O(OPri)", Journal of Solid State Chemistry, 1998, pp. 168-176, vol. 141.

* cited by examiner

*Primary Examiner* — Joseph Kosack
(74) *Attorney, Agent, or Firm* — Westerman, Hattori, Daniels & Adrian, LLP

(57) ABSTRACT

Provided is a method for synthesizing a rare-earth oxo isopropoxide safely with a high yield, using a rare-earth metal, which is more inexpensive than anhydrous rare-earth chlorides, as a raw material.

In a solvent containing 90% or more by weight of isopropyl alcohol, a rare-earth metal and isopropyl alcohol are caused to react with each other in the presence of a mercury compound catalyst, a solvent is added thereto or the solvent is partially replaced, and then in a solvent containing 25% or more by weight of an aromatic hydrocarbon solvent having 6 to 10 carbon atoms or a saturated hydrocarbon solvent having 5 to 12 carbon atoms, water is added to conduct partial hydrolysis reaction, thereby synthesizing a rare-earth oxoisopropoxide.

6 Claims, No Drawings

METHOD FOR SYNTHESIZING RARE-EARTH OXO ISOPROPOXIDE

BACKGROUND OF THE INVENTION

1. Field of the Invention

The present invention relates to a method for synthesizing rare-earth oxo isoproxide ($Ln_5O(O-i-C_3H_7)_{13}$), which is useful as a raw material of a polymerization catalyst or asymmetric synthesis catalyst.

2. Description of the Related Art $La_5O(O-i-C_3H_7)_{13}$ is one species of rare-earth oxo isopropoxide (referred to as $Ln_5O(O-i-C_3H_7)_{13}$ hereinafter, wherein Ln represents a rare-earth element).

$Ln_5O(O-i-C_3H_7)_{13}$ is useful as a polymerization-catalyst starting material. For example, V. Simic, N. Spassky, L G. Hubert-Pfalzgraf, "Macromolecules", 1997, vol. 30, pp. 7338-7340 states that oxo isopropoxide of Y or La can be used for a ring-opening polymerization reaction of a lactide.

$Ln_5O(O-i-C_3H_7)_{13}$ or rare-earth alkoxides beside it are used also as raw materials of various catalytic asymmetric syntheses or polymerization reactions.

About a synthesizing process of $Ln_5O(O-i-C_3H_7)_{13}$, for example, O. Poncelet, W. J. Sartain, L G. Hubert-Pfalzgraf, K. Folting, K. G. Caulton, "Inorganic Chemistry", 1989, vol. 28, pp. 263-267 states that metallic yttrium, and mercuric chloride and mercuric acetate as catalysts are added to a mixed solvent of isopropyl alcohol and toluene, the solution is refluxed to cause reaction, and the resultant is subjected to filtration, recrystallization and drying to synthesize $Y_5O(O-i-C_3H_7)_{13}$ with a yield of 75%.

However, the above-mentioned document O. Poncelet, W. J. Sartain, L G. Hubert-Pfalzgraf, K. Folting, K. G. Caulton, "Inorganic Chemistry", 1989, vol. 28, pp. 263-267 does not describe partial hydrolysis by the addition of water.

The present inventors tried to conduct the same synthesizing process. As a result, the substance obtained by filtrating the reaction liquid, distilling off the solvent from the filtrate and then drying the residue contained a large amount of components insoluble in an organic solvent such as THF or toluene in some cases. Thus, the reproducibility of the solubility of the substance in an organic solvent was poor. Thus, it was difficult to use the substance as a raw material of an organic synthesis catalyst.

Moreover, the above-mentioned document V. Simic, N. Spassky, L G. Hubert-Pfalzgraf, "Macromolecules", 1997, vol. 30, pp. 7338-7340 states that $La_5O(O-i-C_3H_7)_{13}$ was synthesized according to the document O. Poncelet, W. J. Sartain, L G. Hubert-Pfalzgraf, K. Folting, K. G. Caulton, "Inorganic Chemistry", 1989, vol. 28, pp. 263-267, but includes no description about the identification of the product.

The present inventors tried the same synthesizing process. As a result, the concentration of isopropyl alcohol in the reaction solution was as low as 50% so that the induction period, which ends at a time when the reaction starts, was 20 hours or longer. Thus, the reaction efficiency was poor. Furthermore, the reaction liquid obtained by causing metallic lanthanum and isopropyl alcohol to react with each other contained a solid component in a large amount of about 50% by mole of metallic lanthanum used in the reaction. As a result, the yield of $La_5O(O-i-C_3H_7)_{13}$ obtained after the solid component was removed by filtration was from 10 to 40%, so that the productivity was poor.

Furthermore, Tamon Okano et al., "The Journal of the Chemical Society of Japan", 1993, vol. 5, pp. 487-492 describes a process of adding metallic lanthanum in a powdery form and mercuric chloride to isopropyl alcohol, heating and refluxing the solution, and subjecting the resultant to concentration, extraction with benzene, filtration, distillation, drying and recrystallization so as to synthesize $La(O-i-C_3H_7)_3$.

However, this synthesizing process is not based on partial hydrolysis, either, and is a process similar to the processes described in the documents V. Simic, N. Spassky, L G. Hubert-Pfalzgraf, "Macromolecules", 1997, vol. 30, pp. 7338-7340, and O. Poncelet, W. J. Sartain, L G. Hubert-Pfalzgraf, K. Folting, K. G. Caulton, "Inorganic Chemistry", 1989, vol. 28, pp. 263-267. The synthesis yields are also as low as values of 20 to 30%.

Furthermore, JP-A No. 9-157272 discloses a process of adding, to an alcohol, a rare-earth metal and iodine (and a mercuric chloride) as a catalyst to synthesize a rare-earth metal alkoxide. This synthesizing process is not based on partial hydrolysis, either. Moreover, it is unavoidable that the product is contaminated by iodine.

Additionally, G. Westin, M. Kritikos, M. Wijk, "Journal of Solid State Chemistry", 1998, vol. 141, pp. 168-176 describes a process of synthesizing potassium isopropoxide in a mixed solvent of isopropyl alcohol and toluene, adding water to this solution, and then adding anhydrous $ErCl_3$ to the resultant, thereby causing the reactive components to react with each other, thereby synthesizing $Er_5O(O-i-C_3H_7)_{13}$.

However, this process has a problem that the anhydrous rare-earth chloride as the raw material is expensive so that production costs increase.

The document G. Westin, M. Kritikos, M. Wijk, "Journal of Solid State Chemistry", 1998, vol. 141, pp. 168-176 also states that $Er_5O(O-i-C_3H_7)_{13}$ can be synthesized by causing reaction with metallic erbium in a mixed solvent of isopropyl alcohol and toluene, removing the resultant solid component, which has olive color, distilling the supernatant, drying the residue to yield a pink viscous material with a yield of 40 to 45%, and then hydrolyzing this material partially in a mixed solvent of isopropyl alcohol and toluene.

However, in this process, at the time of removing the solid component from the reaction liquid obtained by the reaction between metallic erbium and isopropyl alcohol, the rare-earth element contained in this solid component is also removed so that a poor yield is given. This process is not according to partial hydrolysis of the olive solid component, either. Additionally, the document never refers to $La_5O(O-i-C_3H_7)_{13}$.

In short, it has not been known in the prior art that $La_5O(O-i-C_3H_7)_{13}$ can be yielded by subjecting a solid component obtained by reaction with metallic lanthanum and isopropyl alcohol to partial hydrolysis.

According to reaction between a rare-earth metal and isopropyl alcohol, an unreacted fraction of the rare-earth metal remains as it is in a small amount. In any conventional process, the unreacted rare-earth metal is removed by filtration or decantation. However, the metal is very fine and highly active; thus, when the metal contacts the atmosphere, the metal reacts with oxygen so that the metal ignites immediately. For this reason, in steps in the process, very careful attention is required to be paid.

Furthermore, in the prior art, an unreacted fraction of rare-earth metal has never been inactivated at the same time of synthesizing $Ln_5O(O-i-C_3H_7)_{13}$.

SUMMARY OF THE INVENTION

The present invention has been made to solve the above-mentioned technical problems, and an object thereof is to provide a method wherein a rare-earth metal, which is more inexpensive than anhydrous rare-earth chlorides, is used as a raw material to synthesize $Ln_5O(O-i-C_3H_7)_{13}$ safely with a high yield.

The method for synthesizing $Ln_5O(O-i-C_3H_7)_{13}$ according to the invention includes: adding water to a reaction liquid obtained by causing a rare-earth metal and isopropyl alcohol to react with each other, which contains a solid component, so as to cause partial hydrolysis reaction, thereby producing $Ln_5O(O-i-C_3H_7)_{13}$.

In the case of conducting the partial hydrolysis reaction without removing the solid component nor an unreacted fraction of the rare-earth metal in the reaction liquid as described above, $Ln_5O(O-i-C_3H_7)_{13}$ can safely be synthesized with a high yield.

In the synthesizing method, it is preferred to: add, to the reaction liquid obtained by causing the rare-earth metal and isopropyl alcohol to react with each other, which contains the solid component and the unreacted fraction of the rare-earth metal, water in an amount of 10 to 30% by mole of the rare-earth metal used for the reaction, so as to cause the partial hydrolysis reaction; centrifuge or filtrate the resultant to remove the unreacted fraction of the rare-earth metal; and evaporate the filtrate to dryness, thereby producing $Ln_5O(O-i-C_3H_7)_{13}$.

In the synthesizing method, it is preferred that the rare-earth metal and isopropyl alcohol are caused to react with each other in the presence of a mercury compound catalyst in a solvent containing 90% or more by weight of isopropyl alcohol, a solvent is added thereto or the solvent is partially replaced, and then in a solvent containing 25% or more by weight of an aromatic hydrocarbon solvent having 6 to 10 carbon atoms or a saturated hydrocarbon solvent having 5 to 12 carbon atoms, water is added, thereby conducting the partial hydrolysis reaction.

It is particularly preferred that toluene is used as the aromatic hydrocarbon solvent having 6 to 10 carbon atoms.

The synthesizing method can be preferably applied, in particular, to a case where the rare-earth metal is metallic lanthanum.

As described above, in accordance with the synthesizing method according to the invention, $Ln_5O(O-i-C_3H_7)_{13}$, which is useful as a raw material for organic synthesis catalysts, can be safely synthesized with a high yield by use of a rare-earth metal, which is more inexpensive than anhydrous rare-earth chlorides, as a raw material.

DESCRIPTION OF THE PREFERRED EMBODIMENTS

The invention will be described in more detail hereinafter.

In the method for synthesizing $Ln_5O(O-i-C_3H_7)_{13}$ according to the invention, water is added to a reaction liquid obtained by causing a rare-earth metal and isopropyl alcohol to react with each other, which contains a solid component, so as to cause partial hydrolysis reaction.

In other words, a reaction liquid obtained by causing a rare-earth metal and isopropyl alcohol to react with each other, the reaction liquid thus containing a solid component and an unreacted fraction of the rare-earth metal, is subjected to partial hydrolysis without removing the solid component nor the unreacted fraction of the rare-earth metal from the reaction liquid.

According to the synthesizing method, $Ln_5O(O-i-C_3H_7)_{13}$ can be obtained with a high yield. In addition thereto, about the generated unreacted fraction of the rare-earth metal, the amount of which is small, the surface thereof is hydrolyzed so that the fraction does not ignite immediately even in the atmosphere. As a result, the fraction can safely be disposed of.

The rare-earth metal used for the reaction is preferably in a form having a large specific surface area, such as a powdery form or thin-piece form. When the rare-earth metal contacts the atmosphere, the surface thereof is immediately oxidized with oxygen or water; therefore, it is preferred that the metal is stored in oil just after the metal is worked.

As a solvent for the reaction, isopropyl alcohol is used.

The use amount of isopropyl alcohol is preferably from 2.6 to 260 times the mol number of the used rare-earth metal, more preferably from 13 to 130 times the mol number thereof.

Isopropyl alcohol in this case may be diluted with an aromatic hydrocarbon solvent having 6 to 10 carbon atoms ($C_6$-$C_{10}$), or a saturated hydrocarbon solvent having 5 to 12 carbon atoms ($C_5$-$C_{12}$).

However, if the amount thereof for the dilution is large so that the concentration of isopropyl alcohol becomes too low, the reaction velocity and the reaction rate fall. Thus, the isopropyl alcohol concentration is 50% or more by weight, preferably 90% by weight, more preferably 100% by weight.

Additionally, the rare-earth metal reacts with water and thus an oxide film is formed on the surface so that the metal does not react easily; it is therefore preferred to use a reaction solvent having a water content of 30 ppm or less.

In the above-mentioned reaction, it is preferred that a mercury compound is added as a catalyst. This mercury compound may be mercuric chloride or mercuric acetate.

The mercury compound is preferably added in an amount of 0.1 to 5% by mole of the rare-earth metal. If the mercury compound is not added, the reaction does not advance at all or the reaction rate becomes very low.

The catalyst of the mercury compound is reduced into metallic mercury in the reaction process, and the resultant can be substantially completely removed by filtration.

The above-mentioned reaction is started by adding the rare-earth metal and the mercury compound to the reaction solvent, and then refluxing the solution while stirring the solution.

The reaction period, which is varied in accordance with the kind, the addition amount and the shape of the rare-earth metal and others, is from about 5 to 50 hours.

In a case where the rare-earth metal is lanthanum, metallic lanthanum disappears with the advance of the reaction so as to yield a reaction solution containing a large amount of a gray solid component and an unreacted fraction of the rare-earth metal. In a case where the reaction solvent is made of 100% of isopropyl alcohol, 85 to 95% by mole of metallic lanthanum turns to a solid component.

In a case where the rare-earth metal is a metal other than lanthanum, the rare-earth metal disappears with the advance of the reaction so as to yield a reaction solution containing a small amount of a solid component and an unreacted fraction of the rare-earth metal.

The solid-component-containing reaction solution may be partially hydrolyzed as it is. However, $Ln_5O(O-i-C_3H_7)_{13}$ is slightly soluble in isopropyl alcohol; therefore, in order to conduct the partial hydrolysis uniformly, it is preferred to add thereto a solvent wherein $Ln_5O(O-i-C_3H_7)_{13}$ is easily dissolved, and then conduct the partial hydrolysis.

The solvent to be added to the solid-component-containing reaction solution is preferably a $C_6$-$C_{10}$ aromatic hydrocarbon solvent or a $C_5$-$C_{12}$ saturated hydrocarbon solvent, wherein $Ln_5O(O-i-C_3H_7)_{13}$ is well dissolved. Of the solvents, toluene is particularly preferred.

The addition amount of the solvent is set to such an amount that the concentration of the $C_6$-$C_{10}$ aromatic hydrocarbon solvent or the $C_5$-$C_{12}$ saturated hydrocarbon solvent in all of solvents turns preferably to 25% or more by weight, more preferably to about 50% by weight.

The solid component is slightly dissolved in isopropyl alcohol and in the $C_6$-$C_{10}$ aromatic hydrocarbon solvent or the $C_5$-$C_{12}$ saturated hydrocarbon solvent.

Before the addition of the hydrocarbon solvent, isopropyl alcohol may be partially distilled off.

However, when the amount of the solvent is too small for the solid component in the distillation-off step, the solid component is denatured. As a result, the subsequent partial hydrolysis reaction will not advance. Thus, attention should be paid.

The partial hydrolysis reaction need to be slowly and uniformly conducted. Water to be added is preferably made into the state that the water is diluted with isopropyl alcohol or with a mixed solvent of isopropyl alcohol and toluene. The dilution concentration is preferably 1.0 M or less.

The addition amount of the water is preferably from 10 to 30% by mole of the rare-earth metal used for the reaction, more preferably about 20% by mole thereof.

The partial hydrolysis reaction is advanced by adding the water little by little while stirring the solution at room temperature, and then refluxing the solution.

In a case where the rare-earth is lanthanum, the solid component disappears with the advance of the reaction.

In a case where the rare-earth is an element other than lanthanum, the suspension of the reaction liquid somewhat decreases.

The reaction finishes in a time of 3 to 24 hours.

The reaction liquid after the partial hydrolysis is subjected to filtration, centrifugation or decantation, thereby removing the unreacted fraction of metallic lanthanum and an unreacted fraction of the solid component, and subsequently the filtrate is evaporated to dryness. In this way, $Ln_5O(O-i-C_3H_7)_{13}$, which is a target, is yielded.

$Ln_5O(O-i-C_3H_7)_{13}$ has a very high solubility in hydrocarbon solvent, but is slightly soluble in isopropyl alcohol; therefore, when a solvent wherein these are combined is used as the need arises to conduct recrystallization, a highly pure product can be yielded.

From the viewpoint of safety, it is preferred to subject the residue after the filtration to decomposing treatment immediately since the residue contains fine powder of the rare-earth metal. However, the surface is being hydrolyzed so that the activity thereof is low; thus, even when the residue is allowed to stand still in the atmosphere, the residue does not involve risk of igniting immediately.

In the above-mentioned synthesizing method, it is preferred to conduct all of the syntheses and operations from the reaction to the recrystallization in the atmosphere of an inert gas such as nitrogen or argon.

The invention will be specifically described by way of the following examples; however, the invention is not limited to the examples.

Example 1

Into a 300-mL three-necked flask were added 79 g of isopropyl alcohol, 4.86 g (35.0 mmol) of metallic lanthanum in a thin piece form and 0.03 g of mercuric chloride, and in the atmosphere of nitrogen the flask was heated to 100° C. by use of an oil bath. In this way, the reactive components were caused to react for 12 hours while the solution was refluxed. As a result, a reaction liquid containing a gray solid component was yielded.

Under reduced pressure, 39 g of isopropyl alcohol was distilled off from this reaction liquid at an oil bath temperature of 90° C., and then 43 g of toluene was added thereto.

The solution was cooled to room temperature, and then thereto was dropwise added 7.0 mL of isopropyl alcohol containing 1.0-M water slowly over 20 minutes. Thereafter, the solution was heated at an oil bath temperature of 120° C. and refluxed while stirred for 6.5 hours. As a result, the gray solid component disappeared slowly so as to yield a reaction solution containing unreacted metallic lanthanum powder and a partial unreacted fraction of the solid component.

This reaction solution was filtrated, and then the filtrate was evaporated to dryness, thereby yielding 9.02 g (6.1 mmol) of $La_5O(O-i-C_3H_7)_{13}$ with a yield of 87.2%.

Even when the residue after the filtration was exposed to the atmosphere, the residue did not ignite immediately so that the residue was able to be safely disposed of.

The resultant substance was subjected to ICP-MS analysis. As a result, the La content was 47.1% by weight (theoretical value: 47.0% by weight), and the Hg content was 1 ppm or less.

The molecular weight was measured by the benzene cryoscopic method. As a result, the molecular weight was 1550 (theoretical value: 1478.7). The difference between the measured value and the theoretical value was in a permissible error range.

From these results, the resultant substance was identified as $La_5O(O-i-C_3H_7)_{13}$.

Example 2

Into a 300-mL three-necked flask were added 40 g of isopropyl alcohol, 2.50 g (18.0 mmol) of metallic lanthanum in a thin piece form and 0.02 g of mercuric chloride, and in the atmosphere of nitrogen the flask was heated to 100° C. by use of an oil bath. In this way, the reactive components were caused to react for 12 hours while the solution was refluxed. As a result, a reaction liquid containing a gray solid component was yielded.

To this reaction liquid was added 43 g of toluene, and then the solution was cooled to room temperature. Thereafter, thereto was dropwise added 3.6 mL of isopropyl alcohol containing 1.0-M water slowly over 20 minutes. Thereafter, the solution was heated at an oil bath temperature of 120° C. and refluxed while stirred for 6.5 hours. As a result, the gray solid component disappeared slowly so as to yield a reaction solution containing unreacted metallic lanthanum powder and a partial unreacted fraction of the solid component.

This reaction solution was filtrated, and then the filtrate was evaporated to dryness, thereby yielding 4.78 g (3.23 mmol) of $La_5O(O-i-C_3H_7)_{13}$ with a yield of 89.8%.

Even when the residue after the filtration was exposed to the atmosphere, the residue did not ignite immediately so that the residue was able to be safely disposed of.

Comparative Example 1

Into a 300-mL three-necked flask were added 79 g of isopropyl alcohol, 3.51 g (25.3 mmol) of metallic lanthanum in a thin piece form and 0.02 g of mercuric chloride, and in the atmosphere of nitrogen the flask was heated to 100° C. by use of an oil bath. In this way, the reactive components were caused to react for 12 hours while the solution was refluxed. As a result, a reaction liquid containing a gray solid component was yielded.

Under reduced pressure, 38 g of isopropyl alcohol was distilled off from this reaction liquid at an oil bath temperature of 90° C., and then 43 g of toluene was added thereto.

This was filtered, and then the filtrate was evaporated to dryness, thereby yielding 1.09 g (0.74 mmol) of $La_5O(O\text{-}i\text{-}C_3H_7)_{13}$ with a yield of 14.6%.

This synthesis yield was lower than in Examples 1 and 2. Thus, the present comparative example was poor in productivity.

The residue after the filtration contained unreacted metallic lanthanum fine powder the surface of which was active. When the residue was exposed to the atmosphere, the residue ignited immediately.

Comparative Example 2

Into a 300-mL three-necked flask were added 79 g of isopropyl alcohol, 3.60 g (25.9 mmol) of metallic lanthanum in a thin piece form and 0.02 g of mercuric chloride, and in the atmosphere of nitrogen the flask was heated to 100° C. by use of an oil bath. In this way, the reactive components were caused to react for 12 hours while the solution was refluxed. As a result, a reaction liquid containing a gray solid component was yielded.

The solution was cooled to room temperature, and then thereto was dropwise added 5.2 mL of isopropyl alcohol containing 1.0-M water slowly over 20 minutes. Thereafter, the solution was heated at an oil bath temperature of 120° C. and refluxed while stirred for 6.5 hours.

This was evaporated to dryness, and then the resultant was subjected to extraction with toluene. The resultant solution was evaporated to dryness, thereby yielding 1.49 g (1.01 mmol) of $La_5O(O\text{-}i\text{-}C_3H_7)_{13}$ with a yield of 19.4%.

This synthesis yield was lower than in Examples 1 and 2. Thus, the present comparative example was poor in productivity.

Even when the residue after the filtration was exposed to the atmosphere, the residue did not ignite immediately so that the residue was able to be safely disposed of.

Comparative Example 3

Into a 300-mL three-necked flask were added 39 g of isopropyl alcohol, 43 g of toluene, 4.05 g (29.2 mmol) of metallic lanthanum in a thin piece form and 0.02 g of mercuric chloride, and in the atmosphere of nitrogen the flask was heated to 100° C. by use of an oil bath. In this way, the solution was refluxed for 35 hours, so as to yield a reaction liquid containing a gray solid component. 20 hours were required as a period from the start of the heating and refluxing to the start of the reaction.

This reaction liquid was filtrated to remove the gray solid component, and then the filtrate was evaporated to dryness, thereby yielding 1.87 g (1.26 mmol) of $La_5O(O\text{-}i\text{-}C_3H_7)_{13}$ with a yield of 21.7%.

This synthesis yield was lower than in Examples 1 and 2. Thus, the present comparative example was poor in productivity.

The residue after the filtration contained unreacted metallic lanthanum fine powder the surface of which was active. When the residue was exposed to the atmosphere, the residue ignited immediately.

Comparative Example 4

Into a 300-mL three-necked flask were added 79 g of isopropyl alcohol, 3.72 g (26.8 mmol) of metallic lanthanum in a thin piece form, 0.11 g of mercuric chloride and 5.4 mL of isopropyl alcohol containing 1.0-M water, and in the atmosphere of nitrogen the flask was heated to 100° C. by use of an oil bath. In this way, the solution was refluxed while stirred for 50 hours. However, metallic lanthanum did not react with isopropyl alcohol.

Example 3

Into a 300-mL three-necked flask were added 40 g of isopropyl alcohol, 1.60 g (18.0 mmol) of metallic yttrium in a thin piece form and 0.02 g of mercuric chloride, and in the atmosphere of nitrogen the flask was heated to 100° C. by use of an oil bath. In this way, the reactive components were caused to react for 24 hours while the solution was refluxed. As a result, a reaction liquid containing an unreacted fraction of metallic yttrium was yielded.

To this reaction liquid was added 43 g of toluene, and then the reaction liquid was cooled to room temperature. Thereto was dropwise added 3.6 mL of isopropyl alcohol containing 1.0-M water slowly over 20 minutes. Thereafter, the liquid was heated at an oil bath temperature of 120° C. and refluxed while stirred for 6.5 hours. As a result, a transparent and colorless reaction liquid was yielded which contained a very small amount of an unreacted precipitation of metallic yttrium.

This reaction liquid was filtrated, and then the filtrate was evaporated to dryness, thereby yielding 3.45 g of $Y_5O(O\text{-}i\text{-}C_3H_7)_{13}$ with a yield of 78.0%.

Even when the residue after the filtration was exposed to the atmosphere, the residue did not ignite immediately so that the residue was able to be safely disposed of.

The resultant substance was subjected to ICP-MS analysis. As a result, the Y content was 36.9% by weight (theoretical value: 36.2% by weight), and the Hg content was 1 ppm or less.

The molecular weight was measured by the benzene cryoscopic method. As a result, the molecular weight was 1280 (theoretical value: 1228.7). The difference between the measured value and the theoretical value was in a permissible error range.

From these results, the resultant substance was identified as $Y_5O(O\text{-}i\text{-}C_3H_7)_{13}$.

Example 4

Into a 300-mL three-necked flask were added 40 g of isopropyl alcohol, 3.0 g (18.0 mmol) of metallic erbium in a thin piece form and 0.03 g of mercuric chloride, and in the atmosphere of nitrogen the flask was heated to 100° C. by use of an oil bath. In this way, the reactive components were caused to react for 8 hours while the solution was refluxed. As a result, a reaction liquid containing an unreacted fraction of metallic erbium was yielded.

To this reaction liquid was added 43 g of toluene, and then the reaction liquid was cooled to room temperature. Thereto was dropwise added 3.6 mL of isopropyl alcohol containing 1.0-M water slowly over 20 minutes. Thereafter, the liquid was heated at an oil bath temperature of 120° C. and refluxed while stirred for 6.5 hours. As a result, a transparent and light red reaction liquid was yielded which contained a very small amount of an unreacted precipitation of metallic erbium.

This reaction liquid was filtrated, and then the filtrate was evaporated to dryness, thereby yielding 4.44 g of $Er_5O(O\text{-}i\text{-}C_3H_7)_{13}$ with a yield of 76.2%.

Even when the residue after the filtration was exposed to the atmosphere, the residue did not ignite immediately so that the residue was able to be safely disposed of.

The resultant substance was subjected to ICP-MS analysis. As a result, the Er content was 52.1% by weight (theoretical value: 51.6% by weight), and the Hg content was 1 ppm or less.

The molecular weight was measured by the benzene cryoscopic method. As a result, the molecular weight was 1680 (theoretical value: 1620.4). The difference between the measured value and the theoretical value was in a permissible error range.

From these results, the resultant substance was identified as $Er_5O(O-i-C_3H_7)_{13}$.

What is claimed is:

1. A method for synthesizing a rare-earth oxo isopropoxide, comprising: adding water to a reaction liquid obtained by causing metallic lanthanum and isopropyl alcohol to react with each other, which contains a solid component and an unreacted fraction of metallic lanthanum, so as to cause partial hydrolysis reaction, thereby producing $Ln_5O(O-i-C_3H_2)_{13}$ wherein Ln represents the metallic lanthanum.

2. The method for synthesizing a rare-earth oxo isopropoxide, comprising: adding, to a reaction liquid obtained by causing metallic lanthanum and isopropyl alcohol to react with each other, which contains a solid component and an unreacted fraction of metallic lanthanum, water in an amount of 10 to 30% by mole of metallic lanthanum used for the reaction, so as to cause partial hydrolysis reaction; centrifuging or filtrating the resultant to remove the unreacted fraction of metallic lanthanum; and evaporating the filtrate to dryness, thereby producing $Ln_5O(O-i-C_3H_7)_{13}$.

3. The method for synthesizing a rare-earth oxo isopropoxide according to claim 1, wherein metallic lanthanum and isopropyl alcohol are caused to react with each other in the presence of a mercury compound catalyst in a solvent containing 90% or more by weight of isopropyl alcohol, a solvent is added thereto or the solvent is partially replaced, and then in a solvent containing 25% or more by weight of an aromatic hydrocarbon solvent having 6 to 10 carbon atoms or a saturated hydrocarbon solvent having 5 to 12 carbon atoms, water is added, thereby conducting the partial hydrolysis reaction.

4. The method for synthesizing a rare-earth oxo isopropoxide according to claim 2, wherein metallic lanthanum and isopropyl alcohol are caused to react with each other in the presence of a mercury compound catalyst in a solvent containing 90% or more by weight of isopropyl alcohol, a solvent is added thereto or the solvent is partially replaced, and then in a solvent containing 25% or more by weight of an aromatic hydrocarbon solvent having 6 to 10 carbon atoms or a saturated hydrocarbon solvent having 5 to 12 carbon atoms, water is added, thereby conducting the partial hydrolysis reaction.

5. The method for synthesizing a rare-earth oxo isopropoxide according to claim 3, wherein toluene is used as the aromatic hydrocarbon solvent having 6 to 10 carbon atoms.

6. The method for synthesizing a rare-earth oxo isopropoxide according to claim 4, wherein toluene is used as the aromatic hydrocarbon solvent having 5 to 10 carbon atoms.

* * * * *